United States Patent [19]

Thornton et al.

[11] Patent Number: 5,024,845

[45] Date of Patent: Jun. 18, 1991

[54] METHOD OF REDUCING L-MALIC ACID IN JUICE MEDIUM

[75] Inventors: Roy J. Thornton; Susan B. Rodriguez, both of Palmerston North, New Zealand

[73] Assignee: Massey University, Palmerston, New Zealand

[21] Appl. No.: 337,587

[22] Filed: Dec. 23, 1987

Related U.S. Application Data

[63] Continuation-in-part of Ser. No. 928,432, Nov. 10, 1986, Pat. No. 4,830,968.

[30] Foreign Application Priority Data

Nov. 13, 1985 [NZ] New Zealand .................... 214177

[51] Int. Cl.$^5$ .......................... C12G 1/00; A23L 2/02
[52] U.S. Cl. ................................... 426/15; 426/52; 426/62; 426/599; 435/34; 435/911
[58] Field of Search ................ 426/15, 11, 51, 52, 426/62, 599

[56] References Cited

U.S. PATENT DOCUMENTS

| | | | |
|---|---|---|---|
| 4,547,373 | 10/1985 | Sandine et al. | 426/15 |
| 4,562,077 | 12/1985 | King | 426/15 |
| 4,830,968 | 5/1989 | Thornton et al. | 435/255 |

*Primary Examiner*—Marianne Cintins
*Attorney, Agent, or Firm*—Armstrong, Nikaido, Marmelstein, Kubovcik & Murray

[57] ABSTRACT

A mutant strain of *Schizosaccharomyces* #442 (ATCC46954) requiring both glucose and L-malic acid for growth has been produced which is capable of completely utilising L-malic acid without substantial depletion of glucose. The mutant strain is known as *Schizosaccharomyces malidevorans* Rodriguez-Thornton #11 (ATCC20771). The yeast is capable of being used to remove L-malic acid from mediums including both L-malic acid and glucose thus making it possible to remove L-malic acid from juices without affecting sweetness, or from grape juices during wine-making conditions without affecting the quantities of glucose available for alcohol fermentation.

The invention extends to juice products and wine made using such mutant strains.

9 Claims, No Drawings ial application Ser. No. 928,432, filed Nov.
METHOD OF REDUCING L-MALIC ACID IN JUICE MEDIUM

CROSS-REFERENCE TO RELATED APPLICATION

This application is a continuation-in-part of our earlier U.S. patent application Ser. No. 928,432, filed Nov. 10, 1986 now U.S. Pat. No. 4,830,968.

The present invention relates to improvement in and/or relating to wine-making, novel microorganisms useful in wine-making, screening techniques and plates, etc. enabling identification and separation of microorganisms useful in wine-making, organisms thus separated and their use in wine-making and related means and methods.

There are two major reasons for carrying out a malo-lactic fermentation (MLF) on wines. These are deacidification and microbial stability.

Grapes grown in cool climates, such as New Zealand, make wines of unacceptably high acidity. This problem does not exist in warmer climates, such as Australia, because the grape metabolizes much of the acid and the high sugar level can balance the high acid.

Wine-makers have a choice of biological or chemical deacidification of the wine or juice. They seem to prefer the biological method which involves "encouraging" the growth of lactic acid bacteria in their wines. These bacteria deacidify the wine by converting malic acid to the less strong lactic acid. This conversion is called the malo-lactic fermentation (MLF). Since these bacteria (species of Leuconostoc, Lactobacillus and Pediococcus) are found on grapes and can become part of the winery microflora, some wine-makers depend upon the spontaneous growth of these bacteria in the wine. Other wine-makers purchase cultures of these bacteria with which to inoculate their wines. These bacteria are much more difficult to grow than yeast—temperatures below 60° F. are inhibitory for growth; a sulfur dioxide ($SO_2$) concentration greater than 20 ppm free $SO_2$ could kill the bacteria; a wine which has completed alcoholic fermentation may be too depleted in nutrients to support growth, and there is always the possibility of viral (bacteriophage) attack.

Notwithstanding the sensitivity of ML bacteria to the various factors mentioned previously, most wines can support their growth.

This growth is usually accompanied by the production of carbon dioxide, and this is an obvious problem in packaged wine resulting in "fizzy" bottles and packets of bag-in-the-box still wine. Wines which do not need deacidification are often put through MLF to "stabilise" them, i.e. deplete the malic acid so that the risk of growth of malo-lactic bacteria in the packaged wine is avoided.

Regardless of whether the wine-maker depends upon spontaneous growth of ML bacteria or inoculates with commercially available frozen or freeze-dried cultures, the MLF is a difficult and time-consuming process.

The MLF usually follows the alcoholic fermentation conducted by yeast, and depending upon local conditions, may take from three to twelve weeks to complete. During this period the wine may actually deteriorate in quality since it is still in contact with the yeast cells which are beginning to break down and release cell product into the wine.

Many researchers have attempted to simplify this complex biological deacidification procedure. Some have isolated strains of malo-lactic (ML) bacteria which are more cold tolerant or more $SO_2$ tolerant or go through MLF reliably (Beelman, R. B., A. Gavin II, and R. M. Keen, "A new strain of *Leuconostoc oenos* for induced malo-lactic fermentation in eastern wines", Am. J. Enol. Vitic. 28, (1977) 159–165.; Silver, J., and T. Leighton, "Control of malo-lactic fermentation in wine: Isolation and characterisation of a new malo-lactic organism", Am. J. Enol. Vitic. 32 (1981) 64–72). Others, using the knowledge that yeasts are easier to grow than ML bacteria, have tried to use yeasts which degrade malic acid, e.g. Schizosaccharomyces (Snow, P. G., and J. F. Gallander, "Deacidification of white table wines through partial fermentation with *Schizosaccharomyces pombe*", Am. J. Enol. Vitic. 30 (1979) 45–48) or have attempted to clone the ML bacterial gene into a wine yeast (Williams, S. A., R. A. Hodges, T. L. Strike, R. Snow and R. E. Kunkee, "Cloning the gene for the malo-lactic fermentation of wine from *Lactobacillus delbrueckii* in *Escherichia coli* and yeasts, Appl. Envir. Microbiol. 47 (1984), 288–293). The former method has not been successful because of the variable degree of deacidification (probably due to the fact that Schizosaccharomyces is overgrown by the yeast used for the alcoholic fermentation) and the off-flavours produced. The latter attempt did not work because the genetically engineered yeast did not degrade malic acid to a significant extent.

*Technology of Wine-Making* (4th Edition, Amerine, Berg, Kunkee, Ough, Singleton, Webb, A. V. Publishing Co. Inc., Westport, Conn., U.S.A., 1980, pg 173) identifies Schizosaccharomyces as the name given by Lindner about 1893 to a strain of genus of yeasts known as fission yeasts. Such yeasts multiply in the same manner as bacteria by formation of a transverse wall or septum in the cell and the splitting of the two cells into the two new cells along the line of septum. The yeast described by Lindner was isolated from African beer. Lodder and Kreger-Van (*The Yeasts: A Taxonomic Study*, Ed. 1970, North Holland Publishing Company, Netherlands) states that the genus contains four species namely *Schizosaccharomyces japonicus, Schizosaccharomyces malidevorans, Schizosaccharomyces pombe* and *Schizosaccharomyces octosporus*. The previously referred to articles deal to some extent with the acidification attempts using certain of these species, particularly *Schizosaccharomyces pombe*.

In an article entitled "Decomposition of L-malic acid by wine yeasts" (Journal of Science and Food Agriculture 17 (1966) 312–316) B. C. Rankine discusses the usefulness of a certain strain of *Schizosaccharomyces malidevorans* in decomposing L-malic acid in grape juice. The strain referred to in the article as No. 442 (Rankine) was the only one that gave complete utilisation of L-malic acid and showed no pH dependence. Mutation with ultraviolet irradiation in an attempt to obtain a mutant which would not produce hydrogen sulphide whilst retaining the property of L-malic acid decomposition was unsuccessful.

The strain *Schizosaccharomyces malidevorans* 442, supplied by Dr. B. Rankine of Roseworthy Agricultural College of Advanced Education, South Australia, was used in the mutagenesis which led to the novel strain which constitutes one aspect of the present invention. A similar if not identical organism to that of Dr. Rankine has been deposited at Centraalbureau voor Schimmelcultures as CBS 5557, and is believed to be the same as that deposited with the American Type Culture Collection (ATCC 46954) by Dr. E. Johansen, Microbiology Research Group, Pretoria, South Africa. The microscopic and colonial morphology of the parent strain obtained from Dr. Rankine, that of CBS 5557 and indeed that of the mutated strain (whose microscopic and colonial morphology is not distinguishable from that of the parent strain) are as detailed in the entry for *Schizosaccharomyces malidevorans* in *Yeasts: characteristics and indentification*, Barnett, J. A., Payne, R. W., Yarrow, D. (Cambridge University Press, 1983). The morphology is as follows:

DESCRIPTION

Cream or tan colonies; vegetative reproduction by splitting; no filaments; evanescent asci, containing 1 to 4 smooth, oval or round ascospores.

It should be noted that *Schizosaccharomyces malidevorans* #442 can grow on glucose alone and does not require the presence of L-malic acid for growth.

It is therefore an object of the present invention to provide a method and means for reducing the presence of L-malic acid when in the presence of glucose without a substantial reduction in the level of glucose available for other purposes (such means and methods being applicable in relation to the treatment of juices including the treatment of grape juice in the making of wine).

Accordingly in one aspect the present invention consists in a strain of *Schizosaccharomyces malidevorans* #442 (ATCC46954) which is capable of complete utilising L-malic acid without substantial utilisation of glucose.

Preferably said strain is a mutant obtained by exposure of *Schizosaccharomyces malidevorans* #442 to ultra-

Fermentation

| | | |
|---|---|---|
| 01 D-Glucose + | 05 Sucrose + | 09 Cellobiose − |
| 02 D-Galactose − | 06 ,-Trehalose − | 10 Melezitose − |
| 03 Maltose − | 07 Melibiose − | 11 Raffinose + |
| 04 Me-D-glucoside − | 08 Lactose − | 12 Inulin − |
| | | 13 Starch − |

Growth

| | | |
|---|---|---|
| 14 D-Galatose − | 36 Erythritol − | 58 Cadaverine + |
| 15 L-Sorbose − | 37 Ribitol − | 59 Creatine − |
| 16 D-Glucosamine − | 38 Xylitol − | 60 Creatinine − |
| 17 D-Ribose − | 39 L-Arabinitol − | 61 w/o Vitamins − |
| 18 D-Xylose − | 40 D-Glucitol − | 62 w/o myo-Inositol − |
| 19 L-Arabinose − | 41 D-Mannitol − | 63 w/o Pantothenate D − |
| 20 D-Arabinose − | 42 Galactitol − | 64 w/o Biotin |
| 21 L-Rhamnose − | 43 myo-Inositol − | 65 w/o Thiamin + |
| 22 Sucrose + | 44 D-Glucono- | 66 w/o Biotin & |
| 23 Maltose − | 1,5 lactone + | Thiamin − |
| 24 ,-Trehalose − | 45 2-Keto-D- | 67 w/o Pyridoxine + |
| 25 Me-D-glucoside − | gluconate + | 68 w/o Niacin − |
| − | 46 5-Keto-D- | 69 w/o Folic acid + |
| 26 Cellobiose − | gluconate − | 70 w/o PABA + |
| 27 Salicin − | 47 D-Gluconate D | 71 at 25° C. + |
| 28 Arbutin − | 48 D-Glucuronate − | 72 at 30° C. + |
| 29 Melibiose − | 49 DL-Lactate − | 73 at 35° C. + |
| 30 Lactose − | 50 Succinate − | 74 at 37° C. + |
| 31 Raffinose + | 51 Citrate − | 75 at 42° C. − |
| 32 Melezitose − | 52 Methanol − | 76 0.01% Cycloheximide D |
| 33 Inulin D | 53 Ethanol − | 77 0.1% Cycloheximide − |
| 34 Starch − | 54 Nitrate − | 78 50% D-Glucose + |
| 35 Glycerol − | 55 Nitrate − | 79 60% D-Glucose + |
| | 56 Ethylamine − | |
| | 57 L-Lysine W | |

Additional Characterisrics

| | |
|---|---|
| 80 Starch Formation − | 82 Urea hydrolysis + |
| 81 Acetic acid − | 83 Dizaonium blue − |
| production | reaction |

+ = a score of 2+ or 3+ using Wickerham's scale within 7 days.
D = same score after a delay of 14 to 21 days.
− = failure to grow
W = growth tests with nitrogen sources where done using auxanograms which were examined after 4 days of incubation: clearly visible, dense zone of growth is +, a barely discernible zone is "W".

Other descriptions can be found in Lodder, J., and Kreger-Van, R. J. NJM (EDS) *The Yeasts: A Taxonomic Study*, 2nd Ed., 1970, North Holland Publishing Company, Netherlands.

Please note that two standard texts on the subject of yeast taxonomy, characterisation and identification, namely *The Yeasts* N. J. W. Kreger-van Rij (Editor, Elsevier Science Publishers B. V., Amsterdam (1984) and *Yeasts* J. A. Barnett, R. W. Payne and D. Yarrow, Cambridge University Press, Cambridge (1983) classify *Schizosaccharomyces pombe* and *Schizosaccharomyces malidevorans* as separate species.

violet irradiation and identification and selection on a screen plate.

Preferably said strain is in a substantially pure form and can be grown axenically and designated *Schizosaccharomyces malidevorans* Rodriguez-Thornton #11 (ATCC20771).

In a further aspect the present invention consists in an inoculant for use in the treatment of a juice having both glucose and L-malic acid comprising a strain of *Schizosaccharomyces malidevorans* Rodriguez-Thornton #11 (ATCC20771) which is capable of completely utilising L-malic acid without substantial utilisation of glucose.

Preferably said juice is selected from grape juice, apple juice, orange juice, kiwifruit juice, boysenberry juice or any other like juice.

Preferably said inoculant is for use in wine-making conditions.

Preferably said inoculant is in a storage stable form.

In a further aspect the present invention consists in a method of treating a juice which includes as a step the utilisation of L-malic acid in the juice by a strain of *Schizosaccharomyces malidevorans* #442 requiring both glucose and L-malic acid for growth which is capable of completely utilising L-malic acid without substantial utilisation of glucose.

Preferably said method is a method of wine-making which includes the use of the strain under wine-making conditions.

Preferably the juice is grape juice.

Preferably the strain used in the method is *Schizosaccharomyces malidevorans* Rodriguez-Thornton #11 (ATCC20771).

Preferably the method is performed with the juice being innoculated with the strain at about 25° C. for a period of time prior to inoculation of the juice which will cause alcoholic fermentation.

Preferably the juice is grape juice.

Preferably the L-malic acid utilisation is for a period of about 24 to 36 hours in duration.

Preferably the juice is grape juice and the method is performed in wine-making conditions and the grape juice is substantially simultaneously inoculated with the strain and the yeast used for the alcoholic fermentation so that the utilisation of L-malic acid and the alcoholic fermentation proceeds substantially together although the L-malic acid utilisation will be complete prior to completion of the alcoholic fermentation.

In a further aspect the invention consists in an axenic culture of a strain as previously defined.

In a further aspect the invention consists in *Schizosaccharomyces malidevorans* Rodriguex-Thornton #11 (ATCC20771).

In a further aspect the invention consists in an inoculant for use in reducing L-malic acid in a juice medium comprising a strain of *Schizosaccharomyces malidevorans* #442 (CBS 5557) requiring both glucose and L-malic acid for growth which is capable of completely utilising L-malic acid without substantial depletion of glucose.

Preferably said inoculant is in a storage stable form.

In a further aspect the present invention consists in wine at least substantially devoid of L-malic acid through the inoculation of the grape juice with *Schizosaccharomyces malidevorans* Rodriguez-Thornton #11 (ATCC20771) or a derivative thereof.

In a further aspect the invention consists in a juice product at least substantially devoid of L-malic acid through the inoculation of the juice with *Schizosaccharomyces malidevorans* #11 Rodriguez-Thornton (ATCC20771) or a derivative thereof.

In yet a further aspect the present invention consists in a screen for identifying strains of species of yeast having effective L-malic acid utilisation comprising an inert matrix (preferably agar), L-malic acid, glucose in a concentration greater than 10% by weight, a source or sources of nitrogen and vitamins, and a pH indicator (preferably bromocresol green) which has a gradual colour change over the pH range of about 3 to about 6.5.

In a further aspect the present invention consists in a method of identifying a strain using a screen in accordance with the present invention.

In Totsuka et al. Hakko Kogaku Kaishi, Vol. 59 (3) pp. 231-7 - Abstract (1981) there is described research with a strain of *Schizosaccharomyces pombe* and the fact that *Schizosaccharomyces pombe* #077 cells degraded more L-malic acid when immobilised in a gel than as free cells. There is no implication from the abstract that the fundamental genetic constitution of the cells had been permanently modified such as to increase the ability to utilise L-malic acid or a decreased ability to utilise glucose. This is in contrast with the mutant strain of the present invention which is a mutant of a quite distinct strain from *Schizosaccharomyces pombe* (notwithstanding Sipickzki et al (1982)) and which is one which completely utilises L-malic acid with substantial utilisation of glucose under wine-making conditions and under juice treatment conditions. The strain *Schizosaccharomyces malidevorans* Rodriguez-Thornton #11 (ATCC20771) requires the presence of both glucose and malic acid for growth and cannot grow on either glucose or L-malic acid alone. *Schizosaccharomyces malidevorans* #442 (CBS 5557), the parent or wild type strain, can grow on glucose alone and does not require the presence of L-malic acid for growth.

The physiology of Rodriguez-Thornton strain #11 differs from that of the parent strain supplied by Rankine even though the microscopic and colonial morphology is the same.

Strain #11 can grow aerobically and anaerobically on a medium which contains both malic acid and glucose (or fructose), a nitrogen source and yeast vitamins. This distinguishes strain #11 from its parent since the latter can grow aerobically and anaerobically with glucose as sole carbon source whereas strain #11 requires the presence of both glucose and malic acid for growth. (The ability of strain #11 to ferment and/or assimilate other carbon sources has not been determined, so a complete comparison with the parent strain cannot be made.)

The genetic characterisation of the mutation(s) which cause strain #11 to differ from the parent strain is in progress. It is intended to determine whether (a) the different phenotype is due to mutation in one or more genes and (b) locate the same on the chromosome map of *Schizosaccharomyces malidevorans*.

The nature of the *Schizosaccharomyces malidevorans* mutant that we have isolated is such that it will provide the wine-maker with a viable alternative to the tricky and time-consuming MLF. The reasons for this assertion include:

1. The mutant does utilise far less glucose than the parent strain, although it does require the presence of glucose in order to utilise malic acid. This characteristic means that many of the metabolic pathways are either inactive or have greatly reduced activity and, in doing so, has reduced the number of compounds capable of producing off-flavours.

2. The mutant utilises malic acid at a faster rate than does the wild type *Schizosaccharomyces malidevorans* (within 36 hours at 25° C. in pure culture).

3. The viability of the mutant far exceeds that of the wild type. Thus, the possibility of overgrowth by culture yeast before it has utilised all of the malic acid is much reduced.

4. As the mutant is a yeast there is a much better probability of successfully preparing freeze-dried cultures for inoculation than is the case with ML bacteria.

Wine-making

The present invention also consists in a method of wine-making which includes as a step the utilisation of malic acid by a strain of *Schizosaccharomyces malidevorans* in accordance with the present invention (i.e. a strain of *Schizosaccharomyces malidevorans* or a mutant thereof which is capable of completely or substantially completely utilising malic acid without substantial utilisation of glucose). Preferably the mutant is Rodriguez-Thornton #11 or any other mutant strain isolated using a screening and isolation procedure in accordance with the present invention.

The current process of making red wine (and some white wines) involves an alcoholic fermentation of grape juice by wine yeast followed by a secondary fermentation carried out by the bacterium *Leuconostoc oenos*, which is used to inoculate the wine and in the course of 6 weeks converts malic acid to lactic acid (the malo-lactic fermentation or MLF fermentation). The whole wine-making process may take 8–10 weeks and the MLF is an unpredictable process during which wine spoilage may occur.

Using the yeast strains of the present invention two possible procedures of wine-making are envisaged.

1. Inoculation of grape juice with the mutant followed by incubation at 25° C. for 24–36 hours. In this time all the malic acid would be utilised and the grape juice could then be inoculated with a culture yeast which would carry out the alcoholic fermentation in 10–20 days.
2. Simultaneous inoculation of the grape juice with the mutant and the culture yeast so that malic acid utilisation and alcoholic fermentation proceed together.

It can be seen from the foregoing that it should be possible using the procedures and yeasts of the present invention to carry out the whole double fermentation in approximately 3 weeks compared with 8–10 weeks and this added to the safety factors involved would have obvious cost benefits to wine-makers.

In another aspect the present invention consists in a screen for identifying species of yeast having effective malic acid utilisation comprising an inert matrix, L-malic acid, glucose at a concentration of greater than 10% by weight, a source or sources of nitrogen and vitamins and a pH indicator having a gradual colour change over the pH range of about 3 to about 6.5.

The preferred indicator is bromocresol green indicator although other indicators may also be used.

It is further preferred that the glucose content is greater than 15% by weight, and that the inert matrix is agar.

The procedure by which the preferred form of screen plate is prepared will now be described.

To one liter of agar medium, add 6.7 g Difco Yeast Nitrogen Base (w/o amino acids)
150 g D-glucose
10 g L-malic acid
2.2 ml of a 1% aqueous solution of bromocresol green indicator
500 ml distilled water
Adjust pH to 3.8 using 3N potassium hydroxide.

In a separate flask, mix 20 g agar and 500 ml distilled water.

Autoclave both flasks for 15 minutes at 121° C. (15 psi). Cool both flasks to 50° C., mix the contents together and dispense in 20 ml aliquots into sterile petri dishes. The resulting medium is green.

Colour formation of colonies after 7 days incubation at 30° C. by yeasts utilising different amounts of malic acid in the presence of 10% glucose is as follows:

| Dark blue-green or turquoise | 90% malic acid utilisation | *Schizosaccharomyces malidevorans* |
| --- | --- | --- |
| Dark olive-green | 10–40% malic acid utilisation | *Saccharomyces cerevisiae* |
| Pale green | 80% malic acid utilisation | *Zygosaccharomyces bailii* |
| Light green | 60% malic acid utilisation | *Pachysolen tannophilus* |
| Dark olive-green | 10% malic acid utilisation | *Pichia stipitis* |
| Using the screen plate without glucose gave the following colours after 3 days incubation at 30° C. | | |
| Light blue | 100% malic acid utilisation | *Pachysolen tannophilus* |
| Bright blue | 100% malic acid utilisation | *Pichia stipitis* |

All five yeasts incubated on the screen plate medium without malic acid gave a yellow colour.

It is to be noted that a screen plate in accordance with the present invention has a range of colour changes over the pH range from 3 to 6.5 which is found favourable for identifying good malic acid utilisation with little glucose utilisation.

Using a screen plate in accordance with the present invention strains #11, #34 and #36 Rodriguez-Thornton were isolated. Strain #11 which is the most favoured has been deposited at the American Type Culture Collection as ATCC 20771. The less preferred strains #34 and #36 have not as yet been deposited at ATCC.

In steps prior to the use of the screen plate a centrifuged and washed culture of *Schizosaccharomyces malidevorans* #442 Rankine was resuspended in sterile water and exposed to ultraviolet (UV) irradiation. The irradiated suspension was diluted in sterile water and aliquots spread onto the screen plates. Sixteen light coloured colonies, including strain #11, were subcultured from the screen plates after 5 days incubation at 30° C. Four more light-coloured colonies including strains #34 and #36 were subcultured from the screen plates after a further 24 hours incubation. The remaining light coloured subcultures gave colonies that ranged from light green to turquoise in colour.

The parent strain *Schizosaccharomyces malidevorans* #442 and mutant strains #11, #34 and #36 on the screen plate resulted in blue-green or turquoise colonies (parent) and bright blue colonies (#11, #34 and #36) when incubated on the screen plate at 30° C. for 5 days.

It is believed that repeat mutation of *Schizaccharomyces malidevorans* #442 Rankine or closely similar species such as that deposited at ATCC 46954 together with the use of the screen plate of the invention will result frequently in a mutant strain having substantially the characteristics of Rodriguez-Thornton strain #11 being isolated. Such characteristics are readily recognised on the screen.

On the basis of the foregoing, therefore, it can be seen that by virtue of the use of the Rodriguez screen plate (which forms part of the present invention) novel strains mutated from parent *Schizosaccharomyces malidevorans* can be derived which are complete or at worst substantially complete utilisers of L-malic acid and which do not substantially use glucose even when it is present (which, of course, is the case with the Rodriguez screen plate). With such isolated species (e.g. Rodriguez-Thornton #11 strain and to a lesser extent strains #34 and #36) modified wine-making procedures in accordance with the present invention are possible. Persons skilled in the wine-making business will appreciate how modified yeasts in accordance with the present invention can be marketed for such grape fermentation.

Please note that where other juices are utilised in wine-making conditions then the present invention extends to the inoculation of such juices.

Juice Treatments

The strain and inoculant of the present invention is also useful in reducing the level of L-malic acid present in juices or in any other situation where there is a presence of both glucose and L-malic acid. For present purposes we will confine ourselves to the treatment of juices. The ability of the inoculant of the Rodriguez-Thornton #11 strain to utilise L-malic acid has in addition to grape juice been demonstrated in other juices such as apple, orange, kiwifruit and boysenberry juices and in each case it does not significantly utilise the sugar in these fruit juices. This pattern of utilisation is similar to that observed in grape juice and therefore it is expected that any fruit juice having both glucose and a presence of L-malic acid can be treated with such a strain in order to minimise the L-malic inclusion.

On inoculation with the Rodriguez-Thornton #11 strain the following results were obtained—the L-malic acid being expressed in grams per 100 milli liters of juice.

| Juice | MALIC ACID g/100 ml | |
|---|---|---|
| | Juice Uninoculated | Juice + mutant #11 |
| Apple | 0.55 | ND[a] |
| Orange | 0.44 | ND |
| Kiwifruit | ~0.3 | ND |
| Boysenberry | 0.46 | ND |

Not detected = no malic acid.

It is believed therefore that the strain and inoculants in accordance with the present invention have application in juice treatment and wine-making conditions and indeed can extend into other uses where L-malic acid is to be selectively reduced in the presence of glucose.

What is claimed is:

1. A method for reducing L-malic acid in a juice medium which comprises inoculating the juice medium with a mutant of strain (A) *Schizosaccharomyces malidevorans* #442 (CBS 5557) or (B) as deposited as (ATCC 46954), which mutant requires both glucose and L-malic acid for growth, and which is capable of completely utilizing L-malic acid when grown on a matrix comprising L-malic acid, glucose at concentrations greater than 10% by weight, a nitrogen source, vitamins and a pH indicator having gradual color change over the pH range of about 3 to about 6.5.

2. A method as claimed in claim 1 wherein the strain is *Schizosaccharomyces malidevorans* #11 Rodriguez-Thornton (ATCC 20771).

3. A method as claimed in claim 1 or 2 wherein the juice is grape juice and the inoculation is during a winemaking process.

4. A method as claimed in claim 3 wherein the grape juice is inoculated with the mutant strain at about 25° C. prior to an inoculation of the grape juice with yeast which will cause alcoholic fermentation.

5. A method as claimed in claim 3 wherein the L-malic acid fermentation is for a period of from about 24 to about 36 hours.

6. A method as claimed in claim 3 wherein the grape juice is inoculated with the mutant strain and with yeast used for alcoholic fermentation at about the same time so that fermentations caused by the mutant strain and the yeast proceed simultaneously together although L-malic acid utilization will be complete prior to completion of the alcoholic fermentation.

7. A method as claimed in claim 2 wherein the juice is a fruit juice which is not to be fermented.

8. Wine which has a reduced content of L-malic acid through the inoculation of a grape juice with *Schizosaccharomyces malidevorans* #11 Rodriguez-Thornton (ATCC 20771).

9. A juice product which has a reduced content of L-malic acid through the inoculation of the juice with *Schizosaccharomyces malidevorans* #11 Rodriguez-Thornton (ATCC 20771).

* * * * *